United States Patent [19]

McGredy

[11] Patent Number: Plant 7,319

[45] Date of Patent: Sep. 11, 1990

[54] ROSE PLANT MACMINMO

[75] Inventor: Sam McGredy, Auckland, New Zealand

[73] Assignee: Jackson & Perkins Company, Medford, Oreg.

[21] Appl. No.: 312,963

[22] Filed: Feb. 17, 1989

[51] Int. Cl.[5] ..... A01H 5/00

[52] U.S. Cl. ..... Plt./1

[58] Field of Search ..... Plt. 1

*Primary Examiner*—James R. Feyrer

*Attorney, Agent, or Firm*—Majestic, Parsons Siebert & Hsue

[57] ABSTRACT

A rose variety of the Shrub class is provided having a vigorous arching habit of growth, dark green glossy foilage with bronze colored leaf margins, small brightly colored flowers with unusual distinctive red and white stripes and resistance to disease.

1 Drawing Sheet

SUMMARY OF THE DISCOVERY

The present discovery relates to a new and distinct variety of rose plant of the Shrub class, which was originated by me by crossing an unnamed seedling with the variety Stars 'N Stripes, U.S. Plant Pat. No. 4,029.

The primary objective of this breeding was to produce a new rose variety of the Shrub class displaying vigorous growth and distinctive and unusually colored flowers. This objective was substantially achieved, along with other desirable improvements, as evidenced by the following unique combination of characteristics which are outstanding in the new variety and which distinguish it from its parents as well as from all other varieties of which I am aware. For example, in the pollen parent, Stars 'N Stripes (U.S. Plant Pat. No. 4,029), there are few hips, while the present variety produces ample hips during the year. These hips turn bright orange in the late fall and add to the beauty of this variety. In addition, this variety is distinguished from its pollen parent in that it is of the shrub class and its blooms have distinct bands of red and white color, unlike the pollen parent which is a dwarf of the miniature class and whose color is basically white with red areas bleeding through. Furthermore, this new rose variety has:

1. Vigorous arching habit of growing.
2. Dark green glossy foilage with bronze colored leaf margins.
3. Small brightly colored flowers with unusual distinctive red and white stripes.
4. Resistance to disease.

Asexual reproduction of this new variety by budding and by hardwood cuttings, as performed at Wasco, Calif., shows tha the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose cultivar, which has been denominated "Macminmo". Color terminology is in accordance with The Royal Horticultural Society Colour Chart except where an ordinary dictionary significance for the color is apparent.

Observervations of the buds and flowers were made from specimens grown in a garden environment at Somis, Calif. from May to November.

Flower

The blooming habit is continuous. The bud size is one-half to three-quarters of an inch when the petals start to unfurl. The bud form is a short, pointed ovoid. The bud color when sepals first divide is near Red Group 44A and White Group 155D. Colors are in bands depending on the individual flowers; when half blown the upper side of petals is near Red Group 44A and White Group 155D, in wide and narrow stripes, depending on the individual flower. The lower side of petals is the same. The flowers will fade at the very end, but they drop so quickly that fading goes unnoticed. The sepals have a color near Green Group 137B. The surface texture is covered in fine hairs. There are three normally appendaged sepals, and two unappendaged sepals with hairy edges. The receptacle color is near Green Group 137C. The receptacle has a funnel shape, small size and smooth surface. The peduncle is of short length and glandular surface. Peduncle color is medium green, and the peduncle is stiff and erect.

Bloom

Bloom size is small, with an average open size of two to two and one-half inches, borne several together, in clusters. The clusters are pyramidal. The stems are strong, and long in length. The form when first opened is flat and retained to the end. Under normal conditions there are ten to fifteen petals. The upper side of petals at the flower center is near Red Group 44A and White Group 155D, in broad and narrow bands depending on the flower, and the reverse side of the petals is the same. The base of petals has a small white half moon at the point of attachment. The major color on the upper side is near Red Group 44A and White Group 155D.

There is no fragrance. The petal texture is thin, of a notched, deltoid shape and flat form. The plant has a major bloom in Spring and has scattered blooms the rest of the season.

Pinching spent blossoms can stimulate further flushes of bloom, but because the plant is a shrub, pinching does not altar arching.

The arrangement is imbricated. The blooms drop off cleanly, and last both on the plant and as a cut flower for a fair amount of time.

Reproductive Parts

There are many anthers of medium size. The anthers are yellow and arranged regularly around the styles. The filaments are white, the pollen is gold yellow, the styles are reddish and the stigmas are greenish white.

Plant

A very vigorous growth with arching canes of shrub form. The plant is about five feet high in Southern California. The minimum height is believed to be about three feet high.

Foliage

Small size, of abundant quantity. The new foilage is bronze colored. The old foliage is near Green Group 137A, edged with bronze. Normal mid-stem leaves have five to seven leaflets.

The leaflets are of a pointed oval shape, and have a leathery texture with a serrated edge. The serration is single. Petiole rachis is reddish and petiole underside is smooth with prickles. Stipules are medium to long and bearded. The foliage is resistant to mildew under normal growing conditions as Somis, Calif.

Wood

New wood is light green, with a smooth bark. Old wood is green with a smooth bark.

Prickles

There are many prickles on main canes from the base and many on laterals from the main canes. The form is medium and their shape is straight to hooked slightly downward. There are many prickles on the main stalks and laterals. Color when young is green and turns brown with time.

Other Traits

This variety produces ample hips during the year. These will turn bright orange (Orange-Red Group 32A, color not shown) in late fall (December in California) and add to the beauty of this variety.

Parentage

The seed parent was an unnamed seedling. The pollen parent was the variety Stars 'N Stripes (U.S. Plant Pat. No. 4,029).

Classification

Botanical is Shrub. Commercial is Shrub.

I claim:

1. A new and distinct variety of rose plant of the Shrub class substantially as herein shown and described, characterized particularly as to novelty by the unique combination of red and white striped flowers, glossy green foliage, arching habit of growth and above average disease resistance.

* * * * *

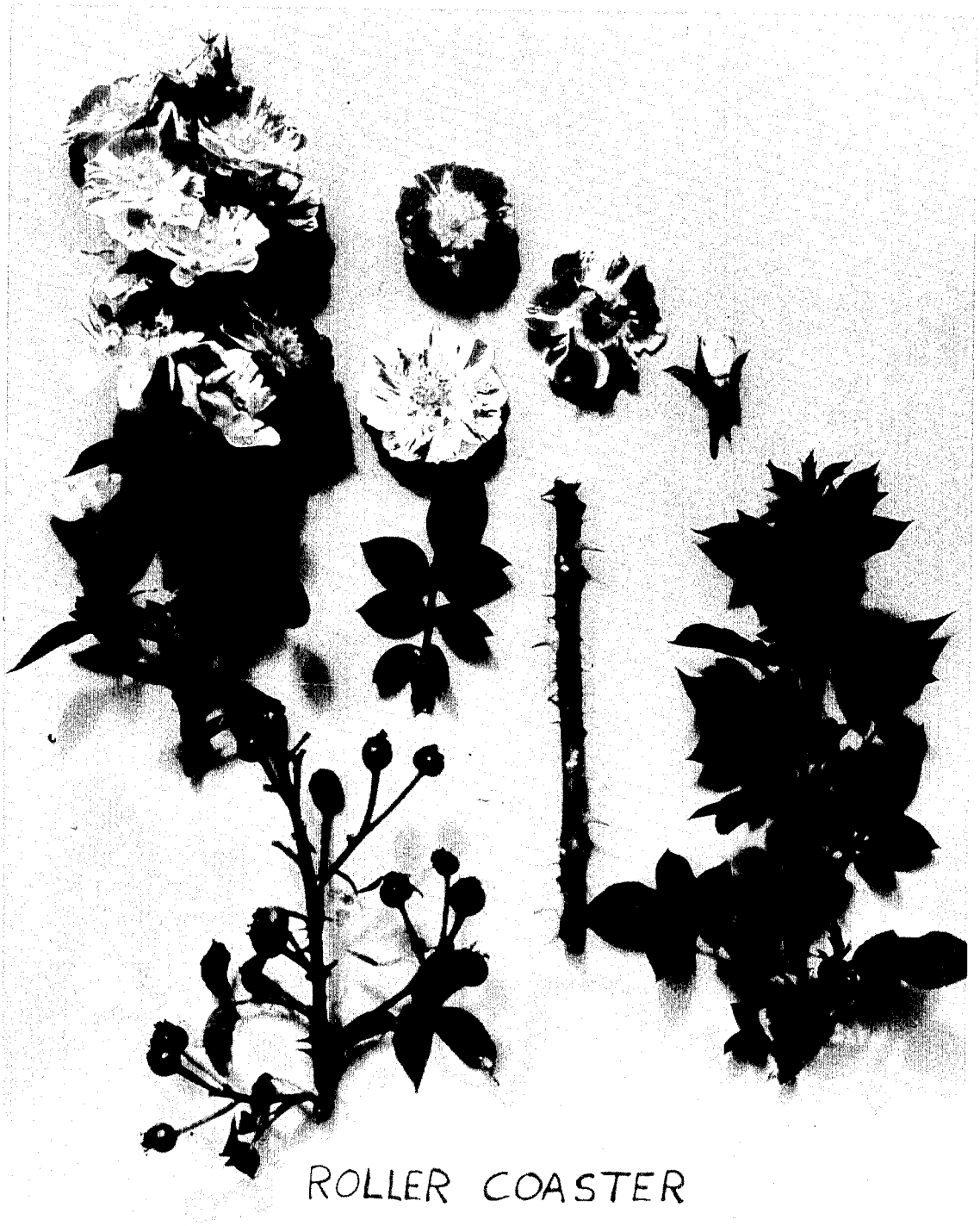
ROLLER COASTER